US 7,167,542 B2

United States Patent
Juschka et al.

(10) Patent No.: US 7,167,542 B2
(45) Date of Patent: Jan. 23, 2007

(54) MOTOR ARRANGEMENT AND METHODS FOR A MULTI-LEAF COLLIMATOR

(75) Inventors: John A. G. Juschka, Eberbach (DE); Björn Werner, Gaussig OT Arnsdor (DE)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 10/951,505

(22) Filed: Sep. 27, 2004

(65) Prior Publication Data

US 2006/0067480 A1    Mar. 30, 2006

(51) Int. Cl.
*G21K 1/04* (2006.01)
(52) U.S. Cl. .................... 378/152; 378/150
(58) Field of Classification Search ............ 378/65, 378/150–153
See application file for complete search history.

(56) References Cited

U.S. PATENT DOCUMENTS

| | | | |
|---|---|---|---|
| 4,672,212 A * | 6/1987 | Brahme ............... | 250/505.1 |
| 4,868,844 A * | 9/1989 | Nunan ................. | 378/152 |
| 4,987,309 A * | 1/1991 | Klasen et al. ........ | 250/492.1 |
| 5,054,041 A | 10/1991 | Hampel | |
| 5,097,131 A | 3/1992 | Plummer et al. | |
| 5,204,892 A * | 4/1993 | Warden ............... | 378/152 |
| 5,727,042 A | 3/1998 | Brenneisen | |
| 5,757,881 A * | 5/1998 | Hughes ............... | 378/65 |
| 6,188,748 B1 * | 2/2001 | Pastyr et al. ........ | 378/151 |
| 6,314,159 B1 | 11/2001 | Siochi | |
| 6,526,308 B1 * | 2/2003 | Heikkinen ........... | 600/436 |
| 6,711,237 B1 * | 3/2004 | Schlegel et al. ..... | 378/152 |
| 6,730,924 B1 * | 5/2004 | Pastyr et al. ........ | 250/505.1 |
| 6,788,764 B1 * | 9/2004 | Saladin et al. ...... | 378/152 |

FOREIGN PATENT DOCUMENTS

WO    WO 031079373    9/2003

* cited by examiner

*Primary Examiner*—Edward J. Glick
*Assistant Examiner*—Thomas R. Artman

(57) ABSTRACT

The motors of a multi-leaf collimator for driving the leaves are tilted away from horizontal. The motors are oriented at an angle upwards from the top or downwards from the bottom of a plane formed by the leaves of the multi-leaf collimator. By tilting or angling the motors relative to the multi-leaf collimator, motors with a single standard or a few different shaft lengths may be used. The motors may be more tightly packed, allowing for shorter leaves. Since Tungsten is expensive, costs may be saved by the shortening of the leaves. Standardization of the motor parts may also reduce costs. Due to the reduced weight of the resulting multi-leaf collimator, wear of the bearings of the linac or gantry arm may be reduced.

21 Claims, 1 Drawing Sheet

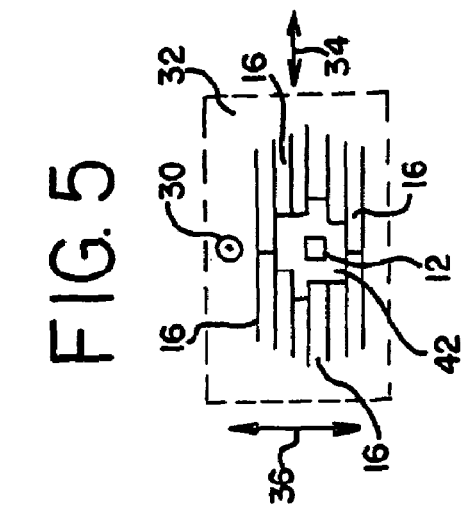
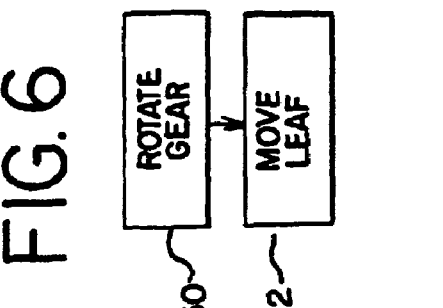
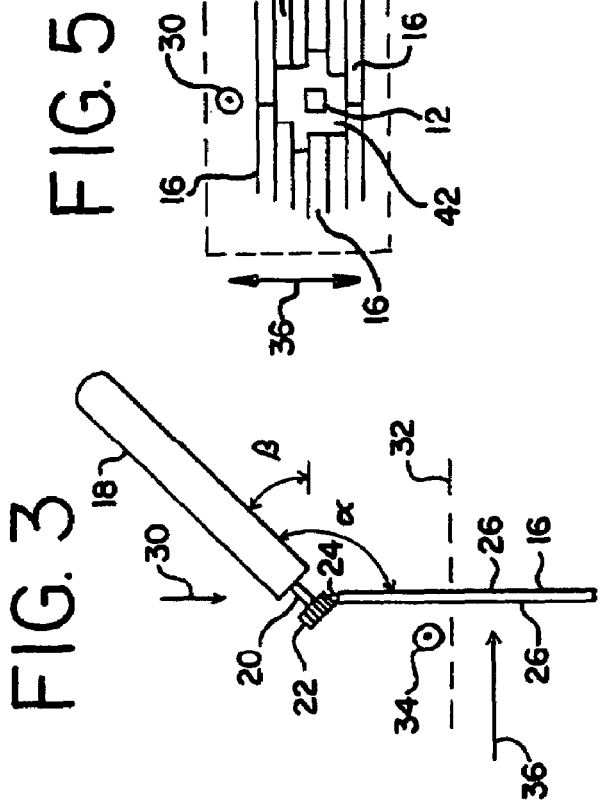
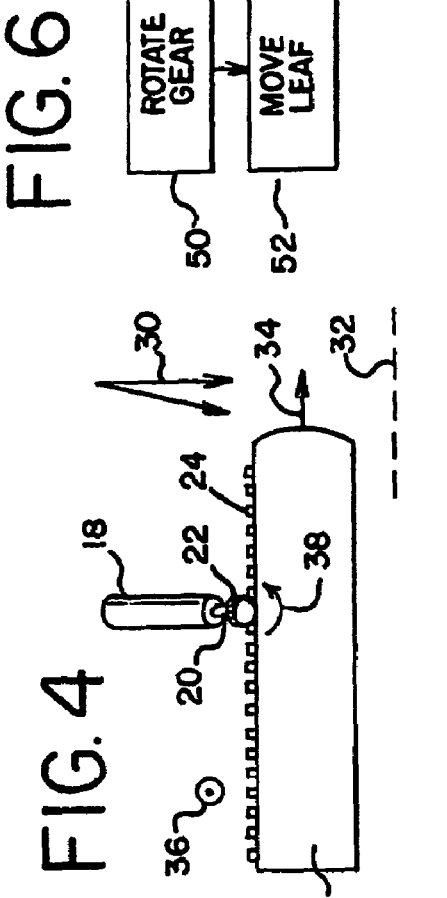
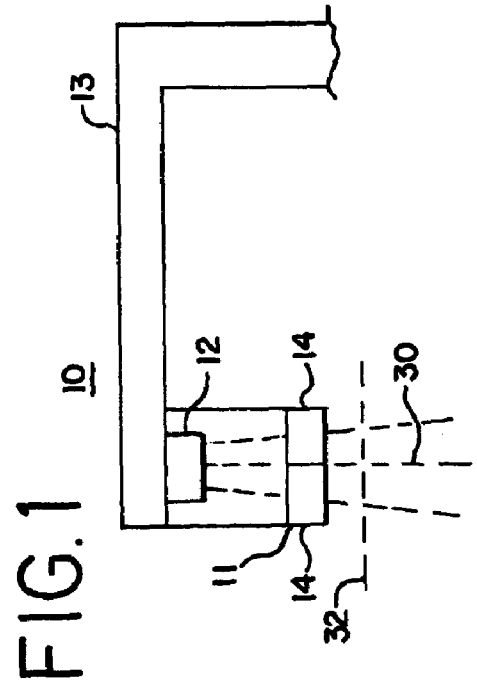
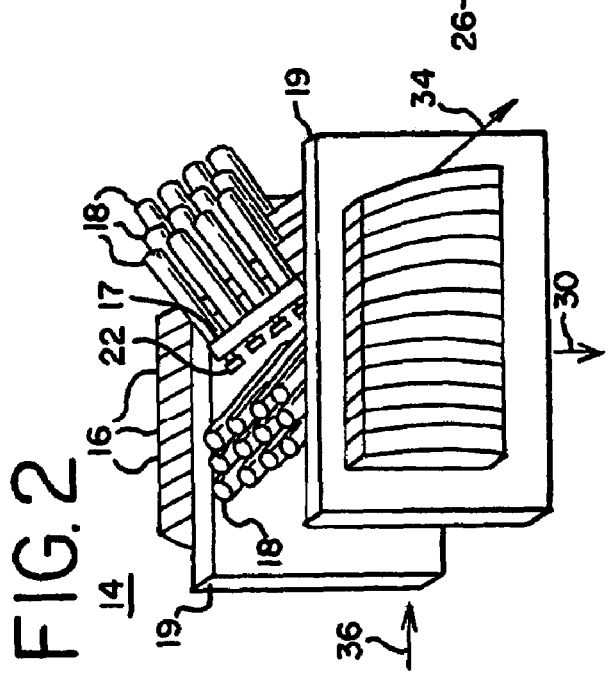

MOTOR ARRANGEMENT AND METHODS FOR A MULTI-LEAF COLLIMATOR

BACKGROUND

The present invention relates to multi-leaf collimators. In particular, an arrangement of motors for moving leafs within a multi-leaf collimator is provided.

The leaves of a multi-leaf collimator are moveable to define an aperture through which radiation passes. Any number of leaves and corresponding motors may be provided, such as 60, 80 or 160. Electronic motors drive the movement or positioning of the leaves.

Where a screw drive motor is used for positioning each leaf, the motor is connected at the end of the leaf opposite the end forming the aperture. By shortening or lengthening the shaft of the motor, the leaf is moved along a same or substantially same axis as the motor shaft.

As an alternative to a screw drive, a gear may be provided on the motors to interact with teeth on each leaf. By rotating the gear, the leaf is moved. The motors are positioned in a plane parallel with the plane defined by the movement of the leaves or the aperture. Where the beam of radiation is directed straight down, the motors are positioned horizontally for moving the leaves in a horizontal direction. Since the leaves of each bank of the multi collimator are positioned in parallel or adjacent to each other, the motors are distributed in a same horizontal plane in staggered positions to provide sufficient space for the motors. As a result of the distribution of motors, each of the leaves is sufficiently long to form the aperture and allow the leaf to be driven by for a motor. Alternatively or additionally, different lengths of motor shafts are provided to allow for a tighter spacing of motors. Using different versions or motor shafts may increase the costs and decrease serviceability.

BRIEF SUMMARY

By way of introduction, the preferred embodiments described below include radiotherapy systems, multi-leaf collimators and methods for controlling a beam of radiation. The motors for driving the leaves are tilted away from horizontal. The motors are oriented at an angle upwards from the top or downwards from the bottom of a plane formed by the leaves of the multi-leaf collimator. By tilting or angling the motors relative to the multi-leaf collimator, motors with a single standard or a few different shaft lengths may be used. The motors may be more tightly packed, allowing for shorter leaves. Since Tungsten is expensive, costs may be saved by the shortening of the leaves. Standardization of the motor parts may also reduce costs. Due to the reduced weight of the resulting multi-leaf collimator, wear of the bearings of the linac or gantry arm may be reduced.

In a first aspect, a multi-leaf collimator is provided for controlling a beam of radiation. A motor has a motor shaft operatively connected with a leaf for moving the leaf. The motor shaft is at an angle greater than 5, 10, 15, 20 or other number of degrees from a plane perpendicular to a center axis of the beam of radiation.

In a second aspect, a multi-leaf collimator is provided for controlling a beam of radiation. A plurality of leaves are moveable along a first axis within a path of the beam of radiation. The leaves are distributed along a second axis substantially perpendicular to the first axis and to a path of propagation of the beam of radiation. Each motor has a shaft operatively connected with one of the leaves for moving the leaf. The motor shaft is at an angle greater than 20 degrees from the first axis and an angle greater than 20 degrees from the second axis.

In a third aspect, a radiotherapy system is provided with a selectable field of application of radiation. A multi-leaf collimator is adjacent to a source of radiation. The multi-leaf collimator includes two banks of leaves operable to define an aperture in a first plane. Two pluralities of motors operatively connect with the respective banks of leaves. The motors are at an angle greater than 20 degrees from the plane of the aperture.

In a fourth aspect, a method is provided for moving a leaf in a multi-leaf collimator. A gear is rotated about the first axis. A leaf is moved along a second axis in response to the rotation of the gear. The leaf has opposite largest surfaces substantially parallel with the second axis. The first axis extends at least 20 degrees from a normal to one of the largest surfaces of the leaf. The normal is perpendicular to the second axis. The first axis is at least within 70 degrees of the normal in a direction along the second axis.

The present invention is defined by the following claims, and nothing in this section should be taken as a limitation on those claims. Further aspects and advantages of the invention are discussed below in conjunction with the preferred embodiments and may be later claimed independently or in combination. Various embodiments of the present invention may have some, none or all of the advantages discussed herein.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 1 is a side view of one embodiment of a portion of a radiotherapy system with a selectable field of application of radiation;

FIG. 2 is a perspective view of one embodiment of a bank of a multi-leaf collimator;

FIGS. 3 and 4 are end and side views of one embodiment of a leaf and associated relationship with a motor of a multi-leaf collimator;

FIG. 5 is a top view of one embodiment of a plurality of leaves of a multi-leaf collimator forming an aperture for application of radiation; and FIG. 6 is a flow chart diagram of one embodiment of a method for moving leaves of a multi-leaf collimator.

DETAILED DESCRIPTION OF THE DRAWINGS AND PRESENTLY PREFERRED EMBODIMENTS

FIG. 1 shows one embodiment of a radiotherapy system 10 with a selectable field of application of x-rays or radiation, such as MeV beams. The radiotherapy system 10 includes a multi-leaf collimator 11, a source of radiation 12, and a gantry arm 13. Additional, different or other components may be provided.

The source of radiation 12 is a rotary radiation head, but other radiation heads for generating radiation may be provided. The source of radiation 12 generates a beam of radiation 30. The beam includes a center axis with diverging outer edges. Convergent or collimated beams may be generated in other embodiments. The beam of radiation 30 is directed through the multi-leaf collimator 11.

The multi-leaf collimator 11 includes two or more banks 14 of leaves for generating an aperture or collimating the beam 30 into a desired pattern for application to a patient. Any number of leaves 16 may be used, such as 60, 80, 160 or other larger or smaller number. A different or same number of leaves 16 are provided for each of the banks 14. The multi-leaf collimator 11 is positioned adjacent to the source 12 of radiation, such as spaced away from the source 12 of radiation by a block collimator or other structures, and connected with the gantry 13 in common with the source 12 of radiation. The banks 14 of leaves of the multi-leaf collimator 11 define an aperture in a plane 32. The plane 32 is perpendicular to the beam of radiation 30, such as shown perpendicular to the center of the beam 30 in FIG. 1, but maybe at another angle. To collimate the beam 30, motors connect with the leaves of each of the banks 14.

FIG. 2 shows one embodiment of one bank 14 of leaves 16 of the multi-leaf collimator 11. The bank 14 includes the leaves 16 positioned through apertures in a frame 19. A plurality of motors 18 are connected to the frame 19 by motor mounts 17. The motors 18 are positioned to interact with respective ones of the leaves 16. Additional, different or fewer components may be provided. For example, additional leaves 16 are provided. As another example, the motors 18 are positioned all at a same angle rather than two different angles. As yet another example, an additional plurality of motors for different leaves connects at one or more angles to the bottom of the leaves 16. The leaves 16 are independently moveable to interfere to in a greater extent or lesser extent with the beam of radiation 30. The direction of the beam of radiation 30 relative to the bank 14 and associated leaves 16 is shown as the arrow labeled 30.

The leaves 16 are in a substantially parallel arrangement. Substantially is used herein to account for the tapering or tapered shape of the leaves 16 from top to bottom as well as manufacturing tolerance. The leaves 16 are placed adjacent to one another and spaced along the axis 36. In one embodiment, the axis 36 is established as perpendicular to the center of the beam of radiation 30 or within the plane 32. Due to any taper of the leaves 16, the axis 36 of the substantially parallel arrangement may be an average of direction of normals to the largest surfaces of the leaves 16. By being positioned in parallel to each other, the leaves 16 may be used to define an aperture for passing the radiation 30 and otherwise blocking the radiation in areas outside of the aperture.

The leaves 16 are operable to extend from and towards the bank 14, such as along the axis labeled 34. The leaves 16 move on bearings, rollers or other structures of the frame 19. Grooves, slots or other structures may be used for guiding the movement of the leaves 16 along the axis 34. The axis 34 is along the direction of movement of the leaves 16 within a path of the beam 30 of radiation. In one embodiment, the axis 34 is perpendicular to the center of the beam of radiation 30 and the axis 36. In other embodiments, the direction of movement 34 is at an angle other than 90 degrees to either or both of the beam of radiation 30 and the axis 36. Any now known or later developed relative arrangement of the leaves 16 relative to each other, such as long axis 36, for movement along the axis 34, and/or relative to the direction of the beam of radiation 30 may be used.

FIGS. 3 and 4 show a single leaf 16 used within the bank 14 of FIG. 2. The leaf 16 is tungsten, an alloy or other material for blocking radiation, such as through absorption or reflection. In one embodiment, the leaf 16 is an elongated plate with one end shaped for the desired reflection or blocking of the beam 30 of radiation. For example, tapers are provided on one end for directing radiation. For positioning adjacent to other leaves 16, leaf 16 has two largest surfaces 26. The two largest surfaces 26 are the same or different size and shape as each other. For example as shown in FIG. 3, one of the largest surfaces 26 is slightly larger than the second largest surface 26 due to the angle of the top of the leaf 16. In one embodiment, the two largest surfaces 26 are parallel to each other. Alternatively, the leaf 16 tapers from a narrowest portion on the top to a widest portion on the bottom. Other variable surfaces may be used for mating with other leaves. Any now known or later developed leaf shape and/or size may be used.

As shown in FIG. 4, the leaf 16 includes a plurality of teeth 24. The teeth 24 act as a gear. The teeth extend along a linear surface of the leaf 16 parallel with the axis of movement of the leaf 34. In alternative embodiments, the teeth 24 are positioned along a non-linear surface. As shown in FIG. 4, the teeth 24 are on a top of the leaf 16. In alternative embodiments, the teeth 24 are on a bottom, side, top or combinations thereof of the leaf 16.

FIG. 2 shows a plurality of motors 18. Each motor 18 connects with a respective one of the leaves 16. The motors 18 rotate the drive shaft 20 in order to move the leaf 16 along the axis 34. The motors 18 are mounted relative to the leaves 16 by the motor mounts 17. Each motor mount 17 is an alloy, stainless steel or other plate or bracket to hold a plurality of motors adjacent to each other and in position adjacent to leaves 16. Bolts or other mechanism are provided for mounting the motors 18 to the motor mounting 17. As shown in FIG. 2, three different sets of parallel plane groupings of motors 18 are formed. Six groupings of motors 18 are shown in two different sets of three parallel groups of motors 18. Additional parallel groupings, different numbers of groupings for different motor orientations, different numbers of motors within a given plane or group, different numbers of motors 18 for different ones of the parallel groupings, or other arrangements of the motors 18 may be provided.

FIGS. 3 and 4 show the motor 18. The motor 18 is a DC, stepper, screw drive or other now known or later developed electronic or hydraulic motor. Each of the motors 18 includes a drive shaft 20 and a gear 22. The gear 22 operatively connects the motor 18 and associated motor shaft 20 with the leaf 16 for moving the leaf 16. The gear 22 includes teeth for mating with the teeth 24 on the leaf 16. In the embodiment shown in FIG. 3, the gearing 22 has teeth that are parallel with an axis formed by the motor shaft 20. The teeth 24 of the leaves 16 are angled at an angle corresponding to the position of the motor shaft 20 and associated motor relative to the leaf 16 for mating the teeth 24 with the gear 22. In alternative embodiments, the gear 22 has teeth at an angle or divergent from parallel with an axis of the motor shaft 20 for mating with the teeth 24. Either one or both of the gear 22 and the teeth 24 are provided at an angle corresponding to the angle of the motor shaft 20 and motor 18 to the leaf 16. Helical gearing may be provided in other embodiments. In yet other alternatives, an additional transmission, gears, belts, rods or other mechanisms may transfer motion of the shaft 20 to movement of the leaf 16.

Referring to FIGS. 2 through 5, the motor 18 and corresponding motor shaft 20 is mounted at an angle relative to the leaf 16. The motor shaft 18 is at an angle greater than 5, 10, 15, or 20 degrees from the plane 32 perpendicular to the center axis of the beam 30 of radiation. For example, the angle is 35–55 or 40–50 degrees, such as being about 40 degrees. Greater or lesser angles may be provided. This angle is represented by β in FIG. 3. Each of the motor shafts 20 of a grouping of motors is at the same angle. In an alternative embodiment, the motor shaft 20 is aligned with the leaf 16 for a 90 degree angle, such as being parallel with the center of the beam 30 of radiation. The teeth 24 of the leaf 16 are positioned on a side of the leaf 16 or other transmission is used to transfer the rotation of the motor shaft 20 to movement of the leaf 16 in a perpendicular direction along the axis 34.

The motor shaft 20 and associated motor 18 are also at an angle greater than 5, 10, 15, or 20 degrees from the direction of movement of the leaf 16 along the axis 34. For example and as shown in FIGS. 2 and 4, the angle of the motor shaft 20 to the direction of movement 34 is about 90 degrees. The motors 18 are substantially positioned within a plane perpendicular to the direction of movement 34. About and substantially allows for angles based on a leaf 16 that moves about a radius rather than along a linear line. The directions over a range of movement of the leaf 16 are averaged to identify an axis or direction of movement. In alternative embodiments, the motor shaft 20 and associated motor 18 are at different angles relative to the axis 34 of movement of the leaf 16. For example, the motor is positioned at 5 degrees, 20 degrees or even in a plane extending in parallel with the axis 34, such as being positioned where the Vector component of the axis of the motor shaft 20 is parallel with the direction of movement 34.

The axis defined by the motor shaft 20 and corresponding motor 18 is at an angle greater than 5, 10, 15 or 20 degrees from the axis 36 extending along the distribution of the leaves 16 within the bank 14. For example, the angle of the motor shaft 20 from the axis 36 is about 35–55 or 40–50 degrees, such as about 40 degrees. Other lesser or greater angles may be provided, including angles less than 20 degrees. An upper or bottom surface formed by the leaves 16 stacked together either as an average where the leaves form a curved surface or as a flat surface defines a plane. The angle of the motor shaft 20 and associated motor 18 is greater than 5, 10, 15 or 20 degrees, such as about 35–55 or 40–50 degrees from the surface or plane. The surface or plane may be parallel or diverged from the plane 32 perpendicular to the beam 30 radiation.

FIG. 5 shows an aperture 42 formed by the leaves 16 being positioned relative to the source of radiation 12. The aperture 42 is formed in a surface or a plane shown or represented by the surface of the page of the figure. The plane is parallel to or diverges from the plane 32 perpendicular to the beam 30 of radiation. The motors 18 and associated motor shafts 20 are at an angle greater than 5, 10, 15, or 20 degrees from the plane formed by the aperture 42. For example, the motor shafts 20 are at an angle about 35–55 or 40–50 degrees, such as 40 degrees, from the plane defined by the aperture.

FIG. 1 shows the gantry 13 in a given position. The gantry 13 may be fixed or movable to various positions. In one position, the beam 30 of radiation is normal to the surface of the earth or substantially intercepts the center of gravity of the earth. The plane 32 is then a horizontal plane. In this relative position of the gantry 13 to the earth, the motors 18 are tilted away from horizontal, such as tilted more than 5, 10, 15 or 20 degrees away from horizontal. Less tilt may be used in other embodiments. One motor 18 may be tilted at greater than 20 degrees while other motors 18 are horizontal or tilted less than 20 degrees.

FIG. 2 shows two sets of motors 18 in the same bank 14. The motors 18 and corresponding shafts 20 are tilted at different angles, such as forming a V shape. Those sets of motors 18 and corresponding motor shafts 20 are at an angle greater than 20 degrees from the plane 32, the plane defined by the aperture 42, and the axis 36 representing the distribution of the leaves 16. In one embodiment, each of the sets of motors 18 is at a same angle, but along a different direction relative to these reference planes or axes. Alternatively, a different, such as larger or smaller angle is provided for one set of motors 18 than the other set of motors 18. In one embodiment, the sets of motors are at an angle of 72–110 degrees from each other within a plane perpendicular to the direction of movement 34 of the leaves 16. Both sets of motors 18 are shown on a top of the leaf 16. In alternative embodiments, one of the sets of motors 18 shown or an additional set of motors 18 are positioned adjacent to the bottom of the leaf 16. The motors 18 are tilted away from the axis 36 and the plane 32 by greater than 20 degrees as discussed above. For example, the motors 18 on the top are about 180 degrees from motors 18 on the bottom within a plane perpendicular to the direction of movement 34. Greater or smaller angles may be provided. Four sets of motors are provided in an alternative embodiment to form two V shapes, one on top and one on bottom of the leaves 16. In yet another alternative embodiment, a single set of motors 18 is provided on either the top or the bottom of the leaves 16.

FIG. 6 shows one embodiment of a method for moving a leaf of a multi-leaf collimator. Additional, different or fewer acts may be provided.

In act 50, a gear is rotated about a first axis. The gear is rotated with a motor having a shaft that extends along the first axis. By spinning the shaft, the gear rotates about the axis.

In act 52, a leaf is moved along an axis in response to the rotation of the gear about the different axes. The leaf includes opposite largest surfaces 26 substantially parallel to the axis or direction of movement. The teeth on the leaf mate with the gear, translating the rotation of the gear into movement of the leaf.

The axis of rotation extends at least 20 degrees from a normal to one or both of the largest surfaces of the leaf along an axis. The normal is perpendicular or substantially perpendicular to the axis or direction of movement. The axis of rotation is within at least 70 degrees of the normal in a direction along the second axis. For example, the axis of rotation of the motor or gear is substantially perpendicular to the direction of movement and is at least 35 degrees from normal to the largest surface of the leaf along another axis.

Twenty degrees, 35–50, 55, 40–50 and 40 degrees are used in the examples above, but greater or lesser angles may be provided. The above described angle is of the tilt of the motor 18 relative to the axis 36, the plane 32 and/or the plane of the aperture 42. The motors 18 are in a plane perpendicular to the direction of movement 34 or perpendicular to the top or bottom surface of the leaf 16. Along the direction of movement 34, the motors 18 may alternatively be tilted. In one alternative embodiment, the tilting described above from the axis 36 or plane 32 is 90 degrees or along a normal line. The angles described above correspond to acute angles or the smallest angle relative to a given reference. In alternative embodiments, the angles may be described as obtuse angles or angles with respect to a given portion of a direction or axis.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A multi-leaf collimator for controlling a beam of radiation, the multi-leaf collimator comprising:
   a collimator leaf operable to move along a leaf axis; and
   a motor having a motor shaft operatively connected with the leaf for moving the leaf, the motor shaft at a first angle greater than 20 degrees from a plane perpendicular to a center axis of the beam of radiation and the motor spaced away from a plane defined by the leaf axis and the center axis of the beam of radiation.

2. The multi-leaf collimator of claim 1 further comprising:
teeth on the leaf; and
a gear on the motor shaft, the gear operable to mate with the teeth.

3. The multi-leaf collimator of claim 2 wherein the leaf is movable along the leaf axis, the teeth are on a linear surface of the leaf parallel with the leaf axis, and one of the gear and the teeth being at a second angle corresponding to the first angle.

4. The multi-leaf collimator of claim 1 further comprising:
a first plurality of leaves including the leaf, the first plurality of leaves in a substantially parallel arrangement; and
a first plurality of motors including the motor, each motor of the first plurality of motors connected with a respective one of the first leaves, respective motor shafts of the first plurality of motors being at the first angle from the plane.

5. The multi-leaf collimator of claim 4 further comprising:
a second plurality of leaves in a same bank as the first plurality of leaves; and
a second plurality of motors, each motor of the second plurality of motors connected with a respective one of the second leave; respective motor shafts of the second plurality of motors being at a second angle greater than 20 degrees from the plane and different than the first angle.

6. The multi-leaf collimator of claim 5 wherein the second angle is about 70–110 degrees from the first angle.

7. The multi-leaf collimator of claim 5 wherein the second angle is about 180 degrees from the first angle.

8. The multi-leaf collimator of claim 4 wherein the first plurality of motors are mounted relative to the first plurality of leaves in at least two parallel groupings of motors.

9. The multi-leaf collimator of claim 1 wherein the first angle is between 35–55 degrees from the plane.

10. The multi-leaf collimator of claim 1 wherein the leaf has a direction of movement along the leaf axis.

11. A multi-leaf collimator for controlling a beam of radiation, the multi-leaf collimator comprising:
a plurality of leaves movable along a first axis within a path of the beam of radiation, the plurality of leaves distributed along a second axis substantially perpendicular to the first axis and to a path of propagation of the beam of radiation; and
a plurality of motors each having a motor shaft operatively connected with one of the leaves for moving the leaf, the motor shaft at a first angle greater than 20 degrees from the first axis and a second angle greater than 20 degrees and within 70 degrees from the second axis wherein the plurality of motors are in groupings of motors, the motor shafts of each grouping being parallel, there being no more than four groupings.

12. The multi-leaf collimator of claim 11 further comprising:
teeth on the leaves; and
a gear on each of the motor shafts, the gear operable to mate with the teeth.

13. The multi-leaf collimator of claim 11 wherein the plurality of motors are mounted relative to the plurality of leaves in at least two parallel groupings of motors.

14. The multi-leaf collimator of claim 11 wherein the first angle is about 90 degrees from the first axis.

15. The multi-leaf collimator of claim 11 wherein the second angle is about 35–55 degrees from the second axis.

16. The multi-leaf collimator of claim 11 wherein the plurality of leaves have a direction of movement along the first axis.

17. A multi-leaf collimator for controlling a beam of radiation, the multi-leaf collimator comprising:
a plurality of leaves movable along a first axis within a oath of the beam of radiation, the plurality of leaves distributed along a second axis substantially perpendicular to the first axis and to a path of propagation of the beam of radiation; and
a plurality of motors each having a motor shaft operatively connected with one of the leaves for moving the leaf, the motor shaft at a first angle greater than 20 degrees from the first axis and a second angle greater than 20 degrees and within 70 degrees from the second axis
wherein a surface formed by the plurality of leaves is substantially perpendicular to the path of propagation of the beam of radiation, wherein the first angle is about 90 degrees from the first axis and wherein the second angle is at about 35–55 degrees from the surface.

18. A radiotherapy system with a selectable field of application of radiation, the radiotherapy system comprising:
a source of radiation; and
a multi-leaf collimator adjacent to the source of radiation, the multi-leaf collimator comprising:
first and second banks of leaves operable to define an aperture in a first plane, each leaf having opposite largest surfaces substantially parallel with an axis of movement; and
first and second pluralities of motors operatively connected with the first and second banks of leaves, respectively;
wherein the motors are at an angle greater than 20 degrees from the first plane and at an angle greater than 20 degrees from the largest surfaces.

19. The radiotherapy system of claim 18 wherein the angle is about 35–55 degrees.

20. A method fat moving a leaf of a multi-leaf collimator, the method comprising:
(a) rotating a gear about a first axis; and
(b) moving a leaf along a second axis in response to (a), the leaf having opposite largest surfaces substantially parallel with the second axis;
wherein the first axis extends at least 20 degrees from a normal to one of the largest surfaces of the leaf the normal perpendicular to the second axis, the first axis being at least within 70 degrees of the normal in a direction along the second axis;
wherein (a) comprises rotating the gear with a motor having a shaft along the first axis, and wherein (b) comprises moving the leaf in response to teeth on the leaf mated with the gear.

21. The method of claim 20 wherein (a) comprises rotating the gear about the first axis, the first axis being substantially perpendicular to the second axis and at least 35 degrees from the normal.

* * * * *